(12) United States Patent
Sägmüller et al.

(10) Patent No.: US 7,923,679 B2
(45) Date of Patent: Apr. 12, 2011

(54) METHOD AND DEVICE FOR HANDLING OBJECTS

(75) Inventors: Bernd Sägmüller, Weilheim (DE); Yilmaz Niyaz, Augsburg (DE); Thomas Staltmeier, Hohenpeissenberg (DE)

(73) Assignee: Carl Zeiss MicroImaging GmbH (DE)

( * ) Notice: Subject to any disclaimer, the term of this patent is extended or adjusted under 35 U.S.C. 154(b) by 473 days.

(21) Appl. No.: 11/916,665

(22) PCT Filed: Jun. 1, 2006

(86) PCT No.: PCT/EP2006/005230
§ 371 (c)(1),
(2), (4) Date: May 23, 2008

(87) PCT Pub. No.: WO2006/131260
PCT Pub. Date: Dec. 14, 2006

(65) Prior Publication Data
US 2009/0045354 A1 Feb. 19, 2009

Related U.S. Application Data

(63) Continuation of application No. PCT/EP2006/005230, filed on Jun. 1, 2006.

(30) Foreign Application Priority Data

Jun. 8, 2005 (DE) .......................... 10 2005 026 540

(51) Int. Cl.
*H05H 3/04* (2006.01)
(52) U.S. Cl. ...................... 250/251; 250/423 P; 250/425; 435/4; 435/40.5; 435/283.1; 356/36; 356/38

(58) Field of Classification Search .................. 250/251, 250/423 P, 425; 435/4, 40.5, 283.1; 356/36, 356/38
See application file for complete search history.

(56) References Cited

U.S. PATENT DOCUMENTS 4,243,887 A * 1/1981 Hillenkamp et al. ...... 250/423 P
(Continued)

FOREIGN PATENT DOCUMENTS

DE 3619062 C2 12/1987
(Continued)

OTHER PUBLICATIONS

Westphal, et al ("Noncontact Laser Catapulting: A Basic Procedure for Functional Genomics and Proteomics" Methods in Enzymology, vol. 356, pp. 80-99, 2002).*

*Primary Examiner* — Robert Kim
*Assistant Examiner* — Michael Maskell
(74) *Attorney, Agent, or Firm* — Mayback & Hoffman, P.A.; Gregory L. Mayback; Rebecca A. Tie

(57) ABSTRACT

In relation with a laser-induced transport process of an object from a carrier to a collecting device, the invention provides a collecting medium in the collecting device in a liquid state. Prior to the laser-induced transport process, the object is separated from a mass on the carrier by laser irradiation. After the laser-induced transport process, the object, thus selected and separated, is transferred together with the collecting medium to a destination, for example, a container, for further treatment. To this end, a manipulation system for liquids is provided, the system permitting manipulation of the collecting medium with the object contained therein with a high degree of reliability and a high throughput.

22 Claims, 5 Drawing Sheets

U.S. PATENT DOCUMENTS

| | | | |
|---|---|---|---|
| 5,348,883 A * | 9/1994 | Togawa | 435/287.3 |
| 5,607,861 A * | 3/1997 | Komatsu et al. | 436/50 |
| 5,623,100 A * | 4/1997 | Arima et al. | 73/611 |
| 5,998,129 A * | 12/1999 | Schutze et al. | 435/4 |
| 6,930,764 B2 * | 8/2005 | Schutze | 356/36 |
| 7,044,008 B1 * | 5/2006 | Schutze et al. | 73/863.01 |
| 7,201,878 B2 * | 4/2007 | Lin et al. | 422/88 |
| 7,438,859 B2 * | 10/2008 | Massaro | 422/100 |
| 7,502,107 B2 * | 3/2009 | Mohanty et al. | 356/317 |
| 2004/0247777 A1 * | 12/2004 | Ringeisen et al. | 427/2.1 |
| 2005/0056782 A1 * | 3/2005 | Shekhawat et al. | 250/306 |
| 2007/0160280 A1 * | 7/2007 | Schutze et al. | 382/133 |

FOREIGN PATENT DOCUMENTS

| | | |
|---|---|---|
| DE | 37 18 066 A1 | 12/1988 |
| DE | 40 04 198 A1 | 8/1991 |
| DE | 196 29 143 A1 | 1/1996 |
| DE | 196 16 216 A1 | 10/1997 |
| DE | 196 29 141 A1 | 4/1998 |
| DE | 198 04 800 A1 | 8/1999 |
| DE | 100 58 316 A1 | 6/2002 |
| DE | 103 22 348 B4 | 5/2005 |
| DE | 103 46 130 A1 | 6/2005 |
| DE | 103 58 565 A1 | 7/2005 |
| DE | 10 2004 041 941 A1 | 3/2006 |
| EP | 1 502 649 A1 | 2/2005 |
| WO | 01/73398 A1 | 10/2001 |
| WO | 02/42824 A2 | 5/2002 |
| WO | 03/029817 A2 | 4/2003 |
| WO | 2006/131260 A2 | 12/2006 |
| WO | 2006/131260 A3 | 12/2006 |

* cited by examiner

METHOD AND DEVICE FOR HANDLING OBJECTS

CROSS-REFERENCE TO RELATED APPLICATION

This is a continuing application, under 35 U.S.C. §120, of copending international application No. PCT/EP2006/005230, filed Jun. 1, 2006, which designated the United States and was not published in English; this application also claims the priority, under 35 U.S.C. §119, of German patent application No. 10 2005 026 540.5, filed Jun. 8, 2005; the prior applications are herewith incorporated by reference in their entirety.

BACKGROUND OF THE INVENTION

Field of the Invention

The present invention relates to a method and a device for handling biological or non-biological objects. The objects can be part of a biological or non-biological mass disposed on a carrier, for example, from which mass it is/they are separated by laser radiation in order to be transported by an ensuing laser-induced transport process to a collecting medium.

For a large number of biological investigations it is necessary to detach individual cells or structures from a united cell structure, such as a tissue or a histological tissue preparation, for instance. This can be carried out, for example, using mechanical microtools, e.g., microcapillaries or microneedles. However, such a procedure is laborious and there is a risk of contamination for the objects removed. Furthermore, such a process can scarcely be automated.

In International publication WO 97/29355 A, corresponding to U.S. Pat. No. 5,998,129 to Schuetze et al., of the applicant, therefore, a new type of method for the sorting and separation of individual biological objects disposed on a planar carrier was proposed. In this method, a selected biological object is separated from the surrounding further biological mass by a laser beam so that the selected biological object is dissected from the remaining biological mass. The thus-exposed biological object is then transferred with the aid of a laser shot or laser pulse from the carrier to a collecting device by a catapult-like process. For this purpose, the collecting device can be a collector substrate, for example, to which the transferred biological object adheres. Furthermore, it is possible to transfer the biological object to a collecting vessel, e.g., a recess or a well of a so-called microtitre tray (or Microtitration Trays as they are sometimes known). An adhesive layer is used preferably to fix the transferred objects on the collector substrate. A UV-absorbent polymer film is used preferably as a carrier for the objects to be transferred or the biological mass from which the objects are separated. However, transport from other carrier substrates, for example, glass, is also possible.

A biological object to be separated from a biological mass placed on a carrier is, thus, first selected with reference to an image of the biological mass, cut out of the biological mass and then transported by a laser-induced transport process to the collecting device. "Biological objects" in the context of the present application are primarily taken to mean, e.g., living or fixed biological cells or cell constituents, which can be part of a liquid or solid biological material, such as a cellular tissue, a smear, a cell culture, or similar.

With the aid of the method described above, defined objects can be removed or separated targetedly from a biological mass. The biological objects can be deposited adjacent one another on a fixed planar carrier, wherein it is possible to carry out the process of removal or separation within a short time and contactlessly. The survivability and the morphology of the biological objects are retained intact depending on the procedure chosen, i.e., the biological objects are not damaged or adversely affected or specifically disintegrated by the separation process and the laser-induced transport process.

For further investigation of the biological objects obtained in this manner, it is necessary to release them from the collector substrate. If the cap of a microcentrifuge tube was selected as a collector vessel, this can be done, for example, in a downstream centrifuging step. Following release from the collector substrate, further processing, e.g., recultivation, can then take place. The biological objects thus come into contact with an additional or intermediate surface in the course of processing. This can cause problems in particular if the intermediate surfaces include or are adhesive materials, such as silicones, PCR oil, plastics, buffer media, etc. On one hand, changes in and/or damage to the biological material can occur. On the other hand, the throughput is reduced by the required release process.

To release living cells from a surface, aggressive solvents (e.g., trypsin) are usually required. Changes in or deterioration of the cells can occur in this process. For example, spontaneous differentiation processes can occur in the treatment of stem cells.

There is a need in the art to provide a simplified and more effective method for handling biological or non-biological objects, in which, in particular, the objects handled can be processed further with a high throughput and a high level of reliability. At the same time, damage to or changes in the objects should be as little as possible and contact with intermediate surfaces should be avoided.

SUMMARY OF THE INVENTION

The invention provides a method and device for handling objects that overcome the hereinafore-mentioned disadvantages of the heretofore-known devices and methods of this general type and that improves upon prior art systems and methods.

Exemplary embodiments of the invention are described below primarily with reference to the handling of biological objects. However, the invention is likewise applicable to non-biological objects (e.g., inorganic materials), these possibly comprising, e.g., microscopically small objects of glass, silica, synthetic material, or artificially produced vesicles in a biological mass. The objects handled according to the invention can, likewise, be removed from a non-biological mass, e.g., a polymer mass or the like.

In the method according to one embodiment of the invention, an object is located on a carrier and is transported by a laser-induced transport process from the carrier to a collecting medium. In an embodiment, the object was cut beforehand by laser radiation from a mass located on the carrier. The collecting medium is in a liquid state. Thus, different liquids can be used as a collecting medium, it being possible for these to have different viscosities provided that a flow motion is possible. The flow motion can be achieved, for example, by a pumping or injection system.

Following the laser-induced transport process, the object is, thus, located in or on the liquid collecting medium. This offers the advantage that the object can be transported advantageously together with the collecting medium for further processing. This can be carried out, for example, by an automatic liquid handling system. In this way, the throughput can be augmented substantially compared with the conventional procedure. Contact of the object with intermediate surfaces is avoided. In particular, the collecting medium is chosen, for example, to be compatible with the further processing, so that the object immediately comes into contact with a liquid relevant for the further processing. Due to suitable conveying of the collecting medium, the object can be transferred directly to a target vessel provided for further processing, e.g., a recultivation vessel.

Furthermore, the method may include a transfer of the object together with the collecting medium to a target location, e.g., into a target vessel. A variety of options exists for this, which can be used jointly or in combination and may guarantee a high throughput. For example, the collecting medium can be put into a flow motion or conveyed actively. A pump system, for example, or acoustic surface waves on a special chip, ultrasonic movement, which is caused, e.g., by a piezo device, or also a laser-induced volume increase (i.e., cavity bubbles) can be used in this case. Furthermore, the collecting medium can be dispensed in drop form into a target vessel, further collecting medium being supplied, for example, from a reservoir to cause a flushing process at the same time and/or to fill the target vessel with collecting medium.

The collecting medium may be held during the laser-induced transport process on a collecting device. Transfer of the object to the target location may then also include a movement of the collecting device relative to the target location. The collecting device may be moved in an automated manner, e.g., by a suitably formed robot.

The device according to an exemplary embodiment of the invention for handling objects can be configured to execute the method described above and includes a collecting device, to which the object is transported by the laser-induced transport process, a holding device for holding the carrier, and a laser configuration for executing the laser-induced transport process. The collecting device is formed to hold a collecting medium, which is in a liquid state. Holding of the collecting medium on the collecting device is achieved, for example, by adhesive force and/or by forces based on the surface tension of the collecting medium.

The device may also include imaging measures for producing an image of the carrier and objects located thereon. With reference to the image of the carrier, it is possible to select objects that are then transported by the laser-induced transport process to the collecting medium. This can take place manually, with the aid of a computer or automatically based on image processing. The imaging measures may be configured, for example, as an inverse or upright microscope or generally include suitable components for an image on a microscopic scale. The imaging measures can also be used advantageously in monitoring the handling process.

According to an exemplary embodiment, the collecting device includes a tip, on which the collecting medium is held in the form of a drop. The tip advantageously includes an opening for dispensing the collecting medium from a reservoir. To provide a liquid surface of the collecting medium suitable for collecting the object, measures can be provided through which an additional surface is provided to hold the collecting medium, and the shaping of the liquid surface for collecting the object can be influenced targetedly. For such a purpose, an inset in the opening of the tip may be provided. Thus, the surface of the collecting medium presented can be influenced targetedly and brought into a suitable shape.

In addition, monitoring measures may be provided, with which the collecting medium is monitored on the collecting device. The monitoring measures can be configured optically and can include a light barrier or an image processing device, for example. Furthermore, the monitoring measures can also be configured so that the monitoring takes place by ultrasound.

With the foregoing and other objects in view, there is provided, in accordance with the invention, a method for handling objects including the steps of locating an object on a carrier and transporting the object by a laser-induced transport process from the carrier to a collecting medium that is in a liquid state.

With the objects of the invention in view, there is also provided a method for handling objects including the steps of locating an object on a carrier, holding a liquid collecting medium on an object collecting device by at least one of adhesion and surface tension, transporting the object from the carrier to the liquid collecting medium by separating the object from a mass located on the carrier with laser irradiation, and following the laser-induced transport of the object, transferring the collecting medium with the object to a target location by drop dispensing the collecting medium.

In accordance with another mode of the invention, following the laser-induced transport process, the object is transferred with the collecting medium to a target location.

In accordance with a further mode of the invention, the transferring step is carried out by conveying of the collecting medium.

In accordance with an added mode of the invention, the transferring step is carried out by causing a flow motion of the collecting medium.

In accordance with an additional mode of the invention, the transferring step is carried out by drop-like dispensing of the collecting medium.

In accordance with yet another mode of the invention, the transferring step is carried out by sucking the collecting medium.

In accordance with yet a further mode of the invention, the collecting medium is held on a collecting device and the transferring step is carried out by moving the collecting device relative to the target location.

In accordance with yet an added mode of the invention, the transferring step is carried out by supplying further collecting medium to the collecting medium with the object.

In accordance with yet an additional mode of the invention, the transferring step is executed automatically.

In accordance with again another mode of the invention, the collecting medium is held on a collecting device by at least one of adhesion and surface tension.

In accordance with again a further mode of the invention, a shaping of a surface of the collecting medium presented to the carrier is influenced targetedly with a geometry of the collecting device.

In accordance with again an added mode of the invention, a shaping of a surface of the collecting medium presented to the carrier is influenced targetedly with a surface composition of the collecting device.

In accordance with again an additional mode of the invention, the collecting medium is selected dependent upon a following processing step for the object.

in accordance with still another mode of the invention, the object is separated from a mass located on the carrier by laser irradiation.

In accordance with still a further mode of the invention, a result of the laser-induced transport process is checked by monitoring the collecting medium.

In accordance with still an added mode of the invention, the monitoring is carried out based upon optical signal processing.

In accordance with still an additional mode of the invention, the checking step is carried out based upon acoustic signals in the ultrasonic range.

With the objects of the invention in view, there is also provided a device for handling objects located on a carrier, including a collecting device configured to hold a collecting medium in a liquid state and to receive objects located on the carrier, a holding device shaped to hold the carrier, and a laser configuration operable to carry out a laser-induced transport process of the objects on the carrier from the carrier to the collecting medium.

In accordance with another feature of the invention, there is provided an imaging device operable to produce an image of the carrier.

In accordance with a further feature of the invention, the collecting device has a tip configured to hold the collecting medium in the form of a drop.

In accordance with an added feature of the invention, the tip has an opening configured to dispense the collecting medium.

In accordance with an additional feature of the invention, the opening of the tip has an inset having an additional surface to hold the collecting medium.

In accordance with a concomitant feature of the invention, the collecting device, the holding device, and the laser configuration are configured to handle the objects on the carrier and transport the objects by the laser-induced transport process from the carrier to the liquid collecting medium.

Other features that are considered as characteristic for the invention are set forth in the appended claims.

Although the invention is illustrated and described herein as embodied in a method and device for handling objects, it is, nevertheless, not intended to be limited to the details shown because various modifications and structural changes may be made therein without departing from the spirit of the invention and within the scope and range of equivalents of the claims.

The construction and method of operation of the invention, however, together with additional objects and advantages thereof, will be best understood from the following description of specific embodiments when read in connection with the accompanying drawings.

As used herein, the term "about" or "approximately" applies to all numeric values, whether or not explicitly indicated. The term "about" generally refers to a range of numbers that one of skill in the art would consider equivalent to the recited values (i.e., having the same function or result). In many instances the term "about" may include numbers that are rounded to the nearest significant figure.

DETAILED DESCRIPTION OF THE INVENTION

Figure 1:
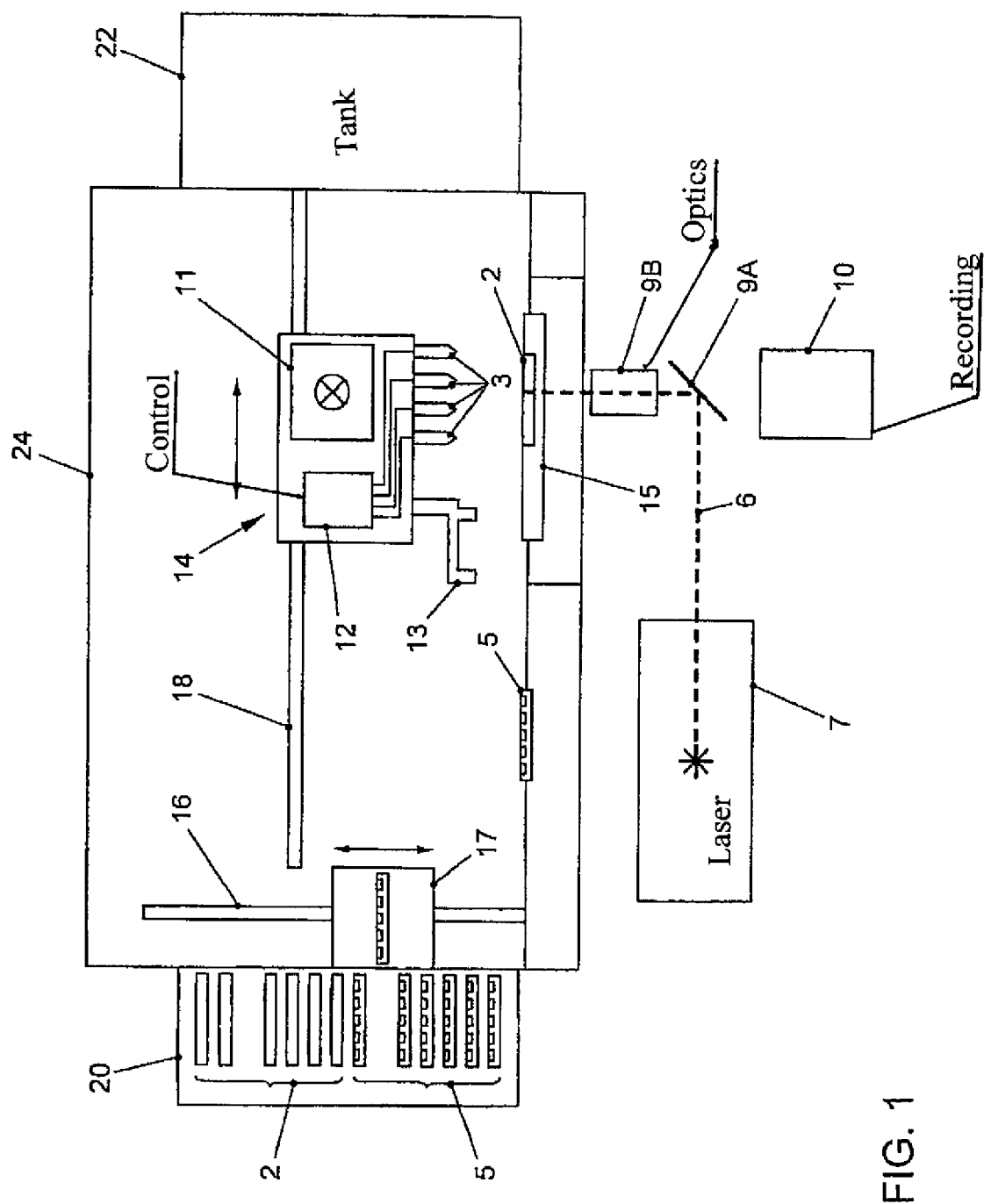
FIG. 1 is a diagrammatic illustration of an overall assembly of a device for handling objects according to an embodiment of the invention.

Referring now to the figures of the drawings in detail and first, particularly to FIG. 1 thereof, there is shown an overall assembly of a device for handling biological objects, which are cut out of a biological mass located on a carrier 2 by laser irradiation. The following embodiments, however, can easily be transferred to the handling of non-biological objects and a non-biological mass. The device is of modular construction and can be adapted individually to different experimental requirements. In the present case, the device includes a microscope structure with an illumination unit 11 and an image recording device 10. The microscope structure is used in a conventional manner to produce an image of the carrier 2 and the objects located thereon. Instead of the inverse microscope structure shown, in which the image recording device 10 is below the level of the carrier 2, the use of an upright microscope structure is also conceivable.

The system shown in FIG. 1 includes a laser device 7 for producing a laser beam 6. The laser beam 6 is coupled into the beam path of the microscope structure through a mirror 9A and optics 9B so that the laser beam 6 can be focused onto the plane of the objects on the carrier 2. In the present case, a pulsed UV laser is used, the wavelength of which is, e.g., 355 nm and the pulse energy of which is, e.g., 150 µJ. The pulse duration is approximately 1 ns, while the pulse frequency can be set between, e.g., 1-200 pulses per second. The laser device 7 can be realized, for example, with a nitrogen laser.

The laser device 7 emits a laser beam 6 of fixed laser energy. The laser beam 6 is used for purposes of so-called laser micromanipulation and laser micro-dissection. For such a purpose, the laser beam 6 is guided in the direction of a motorized and computer-controlled microscope table 15, which serves as a holding device for the carrier 2. The microscope table 15 facilitates exact positioning of the objects located on the carrier 2 with a precision in the nanometer range. Due to the computer-controlled motorization of the microscope table 15, laser-based micromanipulation procedures can be carried out automatically.

The motorized microscope table 15 can be moved along two linear axes (x- and y-direction). The minimum increment size is 20 nm, so that objects on the microscope table 15 can be positioned with a very high level of accuracy. The accuracy and reproducibility of the movement process can be supported or increased by an optical positioning system.

Furthermore, a robotic head 14 is provided, which carries the illumination unit 11 for the microscope structure. The illumination unit 11 may also include a condenser and/or a diffuser of the microscope structure. The robotic head 14 can also be provided with a fine positioning device, which is based, e.g., on piezoactuators and facilitates positioning with increased precision in the nanometer range.

The robotic head 14 carries collecting devices 3 for the collection of objects, which are catapulted from the carrier 2 by a laser-induced transport process in the direction of the robotic head 14. The collecting devices 3 are mounted on the robotic head 14 in a movable manner so that they can be positioned like the microscope table 15 in the x- and y-directions. In addition, mobility in the vertical direction or z-direction is also provided.

The robotic head 14 also includes a gripping device 13, by which the carrier 2 can be gripped on the microscope table 15. The gripping device 13 is equipped with suitable vertical and horizontal mobility for this function. The gripping device 13 is, thus, suitable for loading and unloading the microscope table 15 with the carrier 2. In addition, the gripping device 13 is also suitable for gripping a target vessel 5 and conveying it into a position provided for the vessel 5.

Both the carriers 2 with the biological mass located thereon and the target vessels 5 are kept in an incubator 20, which has a plurality of receiving positions. The receiving positions of the incubator 20 are suitable both for the target vessels 5 and for the carriers 2. This flexibility is accomplished, for example, by having both the carrier 2 and the target vessel 5 correspond in their outer dimensions to a standard microtitre tray and are accommodated in a receiving device with corresponding dimensions. The incubator 20 is provided with a loading and unloading device 17, which is displaceable along a rail 16 in the vertical direction and can remove the carriers 2 and the target vessels 5 automatically from the incubator 20 or insert them therein.

Thus, in the device shown in FIG. 1, both the carriers 2 and the target vessels 5 can be exchanged in an automatic manner. For the automated handling of the carriers 2 and the target vessels 5, the robotic head 14 can be moved horizontally along a rail 18.

Furthermore, the device includes a cooling tank 22, in which heat-sensitive or perishable process media are kept. In particular, a liquid collecting medium or collecting fluid may be kept in the cooling tank 22, which medium is used to collect the objects catapulted from the carrier 2. To this end, the liquid collecting medium is drawn up into the collecting devices 3 formed as nozzles and positioned in the form of a drop relative to the carrier 2. Due to the laser-induced transport process, an object is transported from the carrier 2 into or onto the drop of the collecting medium on the tip of the collecting device 3. Then the tip of the collecting device 3 is positioned above the target vessel 5 and the object is transferred by a targeted drop-like dispensing of the collecting medium from the tip of the collecting device 3 into the target vessel 5. To achieve the drop-like dispensing of the collecting medium from the tip of the collecting device 3, the robotic head 14 is provided with a control and actuation device 12 for the collecting devices 3 configured as nozzles. With the control and actuation device 12, a predetermined amount of collecting medium can be dispensed for each of the collecting devices 3 from an opening located on its tip so that the drop is detached from the collecting device 3 and, in an exemplary embodiment, further collecting medium is supplied to achieve a flushing process. Naturally, a jet-like dispensing of the collecting medium is also possible.

The entire configuration including the robotic head 14, the microscope table 15, and the target vessel 5 is located under a so-called laminar flow box 24, in which, for reasons of cleanliness, a laminar air flow is conducted over the components of the device. However, the device may be structured such that the laminar air flow is deflected in the area below the robotic head 14 so that the laser-induced transport process is not adversely affected by the air flow.

The procedure for automatic handling of objects by the overall assembly shown in FIG. 1 is explained in greater detail below.

First objects to be separated for the procedure are selected with reference to an image of the biological mass on the carrier 2 produced by the microscope structure. This may take place with the aid of a computer as proposed in International Publication WO 01/73398 A of the applicant, corresponding to U.S. Pat. No. 7,044,008 to Schuetze et al., or automatically based upon electronic image processing. If necessary, the selected objects are separated from the mass on the carrier 2 by laser radiation, i.e., micro-dissection is carried out. The separation may be carried out by moving the carrier 2 relative to the laser beam 6 with the microscope table 15 so that the laser beam circumscribes a selected area on the carrier to expose an object contained therein. Suitable control of the laser beam 6 can also be carried out, for example, by a scanning system with a so-called salvo or prism scanner. Then, the laser-induced transport process of the object from the carrier 2 to the collecting device 3 takes place. For such a purpose, the laser beam is directed onto a suitable target point of the object and a laser pulse or laser shot is discharged, which transports the object from the carrier 2 to the collecting device 3. Because the transport takes place in the manner of a pulse or catapult due to irradiation with the laser beam (i.e. ballistic flight occurs following an acceleration phase, which flight is substantially only influenced by the surrounding medium (typically air)), it is possible to speak of catapulting of the object respectively irradiated by the laser beam.

Figure 2:
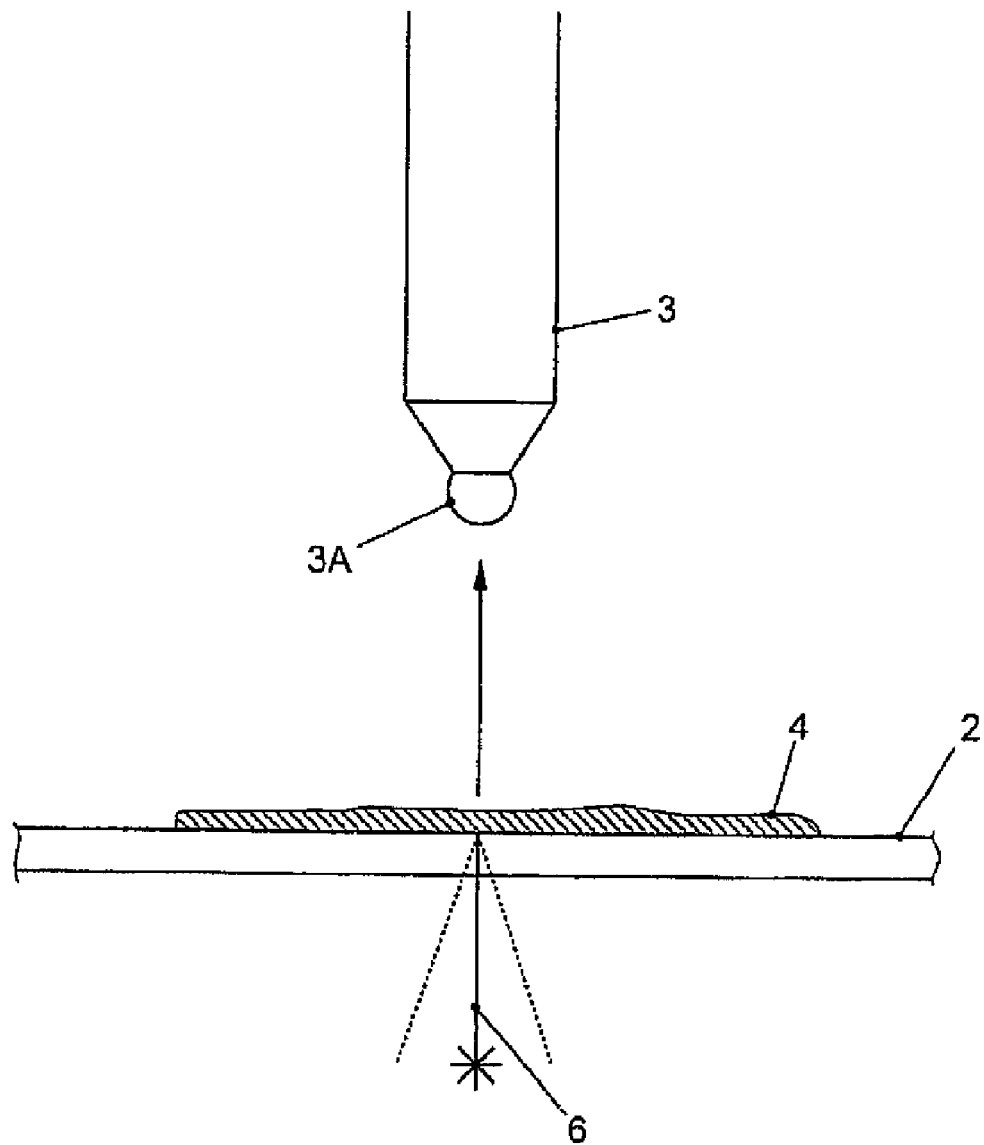
FIG. 2 is a fragmentary, enlarged, diagrammatic illustration of a laser-induced transport process from a carrier to a liquid collecting medium according to the invention.

FIG. 2 shows schematically the configuration of carrier 2, biological mass 4 located thereon and collecting device 3 during the laser-induced transport process. As already mentioned, the laser beam 6 is directed onto a suitable target point and a laser pulse or laser shot is discharged. Due to this action, the selected object is catapulted from the carrier 2 to the collecting device 3, as illustrated by the arrow in FIG. 2. The collecting device 3 is configured as a nozzle, in which a reservoir is located with collecting medium 3A. At the tip of the collecting device 3 is an opening through which the collecting medium 3A can be dispensed. During the laser-induced transport process, a defined quantity of collecting medium 3A is held in the form of a drop on the tip of the collecting device 3. This drop serves as a target for the laser-induced transport process.

Due to automatic execution of a list of positions on the carrier 2, a fixed number of objects may be cut out of the mass 4 and catapulted into the drop of the collecting medium 3A. Depending on the surface tension of the collecting medium 3A and on the nature of the objects catapulted, the objects can remain on the surface of the drop, where they stick due to adhesion.

Figure 3:
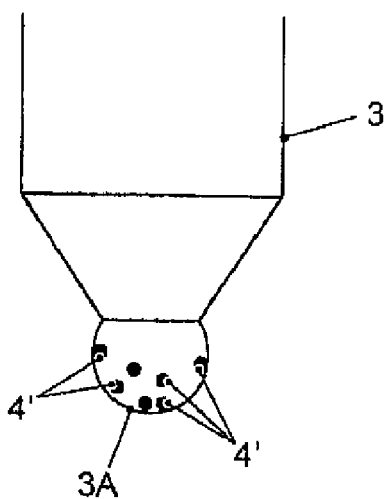
FIG. 3 is a fragmentary, enlarged, diagrammatic illustration of the collecting medium of FIG. 2 with objects contained therein.

FIG. 3 shows the drop of collecting medium 3A located on the tip of the collecting device 3 with the objects 4' located therein. The collecting device 3 is moved in this state by the robotic head 14 to the target vessel 5.

Figure 4:
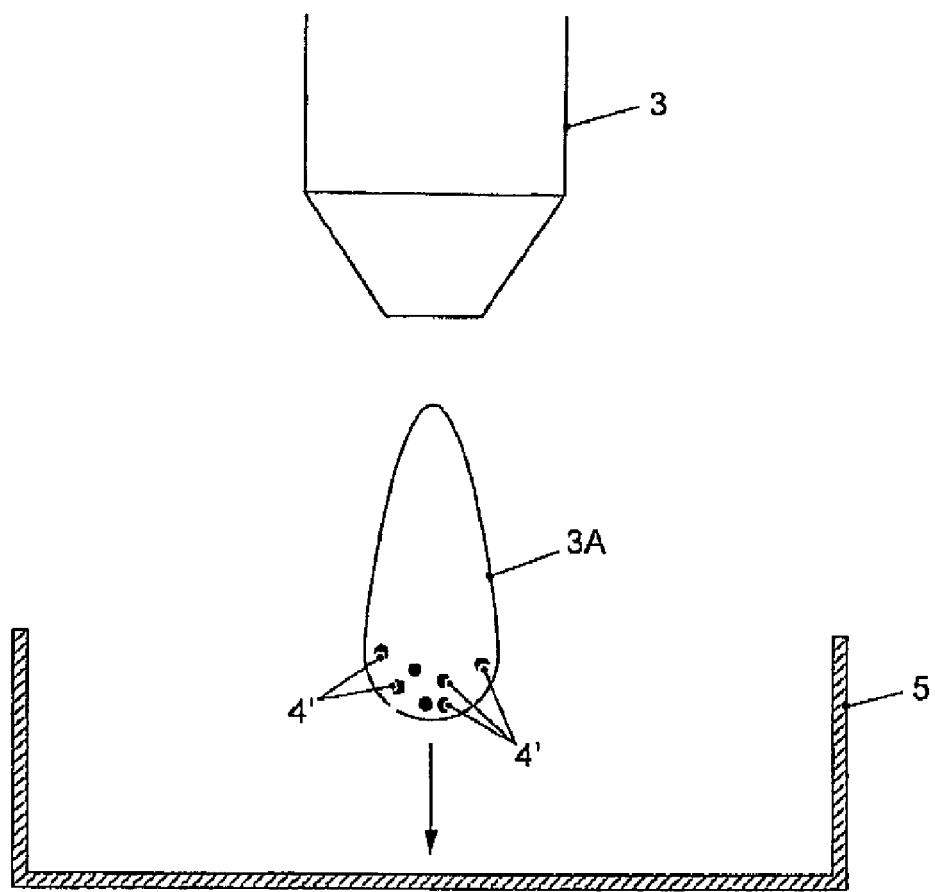
FIG. 4 is a fragmentary, enlarged, diagrammatic illustration of transfer of the collecting medium with the objects contained therein of FIG. 3 to a target location.

FIG. 4 illustrates the discharge of the objects 4' into the target vessel 5. To this end, a predetermined quantity of collecting medium may be dispensed targetedly from the collecting device 3 so that the drop of collecting medium 3A detaches from the collecting device 3 and falls into the target vessel 5. Further collecting medium 3A may also be supplied from the collecting device 3 to flush the collecting device 3 and/or to fill the target vessel 5 with the collecting medium 3A for a further processing step. The latter is particularly advantageous if the collecting medium 3A is compatible with the following processing step or represents a preferred carrier solution for this processing step.

Subsequently further steps can be taken to select and separate objects. The same collecting device 3 can be used for this, or the collecting device 3 can be exchanged. The robotic head 14 may contain several collecting devices 3, which can be filled for example with different types of collecting medium 3A, so that they are suitable for different following processing steps.

The target vessel 5 can, for example, be a so-called microtitre tray with six recesses or wells, which may be suitable for recultivation. Alternatively, it can be a so-called petriperm dish. The collecting medium 3A can be a denaturing liquid, for example, or another process liquid, e.g., a medium for living cells.

The process described above can also include further production of images of the carrier 2 to monitor whether or not the laser-induced transport process was successful. For this, it can be checked in the image of the carrier 2 (for example, at the end of a series of micro-dissection processes with subsequent laser-induced transport process) whether or not the selected objects were successfully removed. In addition, a photograph of the target vessel can be taken to determine whether or not all selected objects were transferred into the target vessel 5. Moreover, optical monitoring of the collecting medium 3A may take place at the collecting device 3. Documentation regulations for the medical sphere, for example, 21 CFR 58.185 and 21 CFR 58.195, can be taken into account in this way.

The collecting medium 3A is held on the collecting device 3 due to adhesion and/or surface tension. For this purpose the collecting device 3 is provided with a suitable geometry. In addition, holding of the collecting medium 3A can be influenced by the surface composition of the collecting device 3 or of its tip. Possible exemplary geometries for the tip of the collecting device 3 are shown in FIGS. 5A and 5B.

Figure 5A:
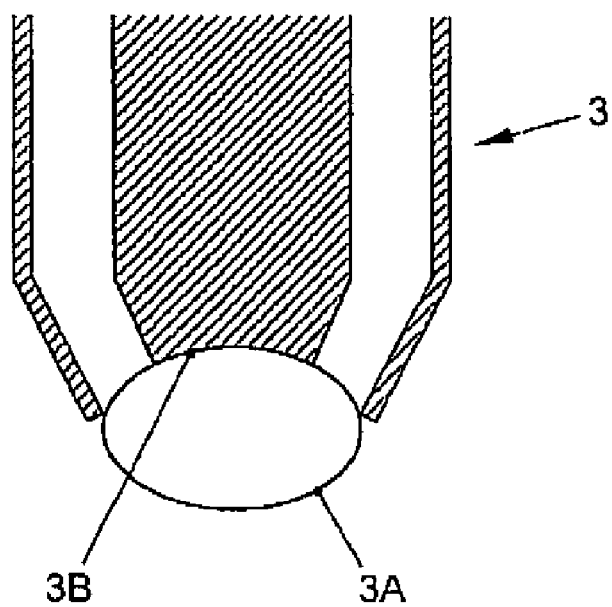
FIG. 5A is a fragmentary, enlarged, diagrammatic illustration of an exemplary collecting device according to the invention on which the liquid collecting medium is held.

FIG. 5A shows a tip which is configured to hold a drop of collecting medium 3A with an enlarged lateral dimension. The enlarged lateral dimension of the drop has the effect that the target accuracy of the laser-induced transport process is less critical. The tip of the collecting device 3 has a generally cylindrical shape, which tapers in an end region close to the tip. The tip ends with a generally circular opening, through which the collecting medium 3A can be dispensed and which serves to receive the drop of collecting medium 3A. Inside the tip is a duct for feeding the collecting medium 3A. Disposed in the middle of the duct is an inset 3B, which has an end surface located in the area of the opening of the tip. The end surface of the inset 3B acts as an additional holding surface for the drop of collecting medium 3A. Furthermore, the shaping of the drop of collecting medium 3A can also be influenced through the positioning of the end surface of the inset 3B and its shape.

Figure 5B:
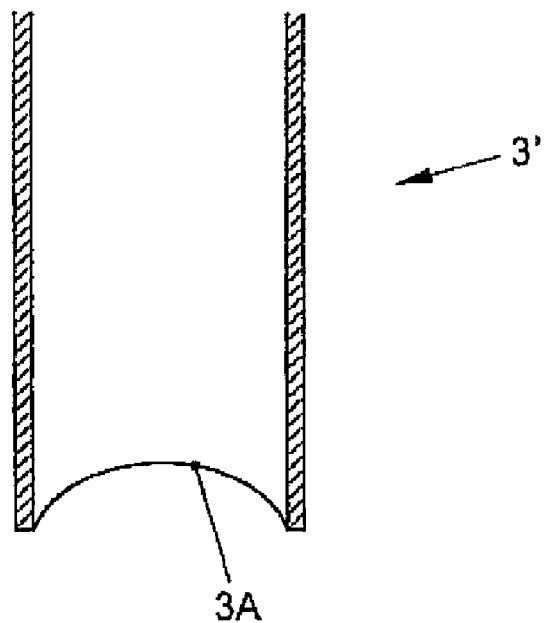
FIG. 5B is a fragmentary, enlarged, diagrammatic illustration of another exemplary collecting device according to the invention on which the liquid collecting medium is held.

FIG. 5B shows a tip of an alternative collecting device 3'. In this case, a substantially cylindrical configuration of the tip is provided, the inner surfaces of the tip configured in the shape of a tube having a surface composition that causes the formation of an inwardly curved meniscus of the collecting medium 3A in the tip. The shape of the surface of the collecting medium can be influenced by suitable measures. Thus, a high affinity of the inner surface of the tip with reference to the collecting medium 3A causes an inwardly curved meniscus, as shown in FIG. 5B. Conversely, an outwardly curved meniscus can be achieved by a reduced affinity of the inner surface of the tip with reference to the collecting medium 3A.

Naturally it is also possible to combine the inset 3B described with reference to FIG. 5B with a targeted setting of the surface affinity. Thus the shaping of the surface of the collecting medium 3 presented to the carrier 2 can be influenced targetedly through the geometry or the surface composition of the collecting device 3.

Figure 6:
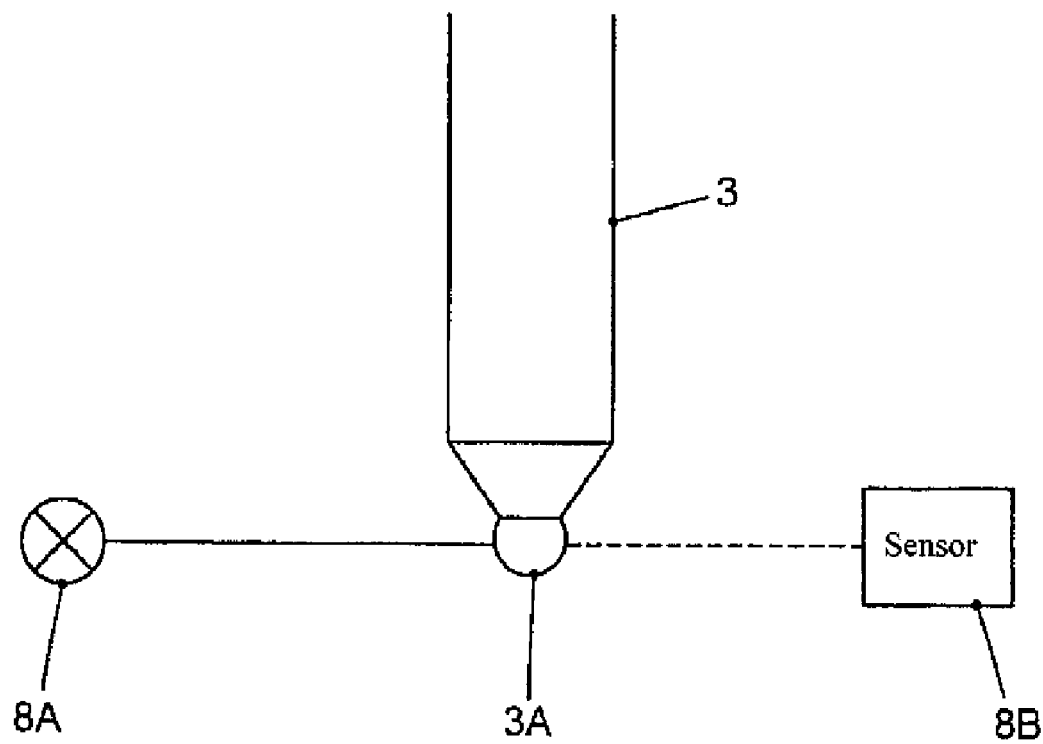
FIG. 6 is a fragmentary, enlarged, diagrammatic illustration of a collecting medium monitoring system according to the invention.

FIG. 6 illustrates schematically monitoring of the collecting medium 3A on the collecting device 3. The monitoring measures shown schematically in FIG. 6 include a light barrier, which has a light source 8A and a sensor 8B. The drop of collecting medium 3A is positioned in the light path so that the signal strength detected by the sensor 8B changes depending on the loading of the drop with objects. Furthermore, in this way whether or not a drop of collecting medium 3A is present on the tip of the collecting device 3 can also be checked. The latter can be used to ensure also that sufficient collecting medium 3A is present on the tip of the collecting device 3 prior to the laser-induced transport process. Furthermore, in this way, the process of dispensing the collecting medium 3A into the target vessel 5 illustrated with reference to FIG. 4 can also be monitored.

Alternative configurations of the monitoring measures can be based, for example, on optical imaging of the collecting medium 3A using automatic image processing or on an ultrasound-based monitoring method.

Furthermore, various options exist for configuring the transport of the separated objects by the collecting medium 3A. Thus, alternatively or in addition to the drop-like transfer of the collecting medium 3A into the target vessel 5 explained with reference to FIGS. 3 and 4, a number of further approaches can be followed. These can include conveying of the collecting medium 3A, evacuation by suction of the collecting medium 3A or a flow movement achieved in another way. The collecting medium 3A can also be transported on special chips by acoustic surface waves. Thus, a direct feed of the collecting medium 3A with the objects 4' contained therein on an analysis chip is possible for certain applications.

The concept described previously of catapulting onto or into a liquid collecting medium is by no means limited to a stationary collecting medium, for example, in the form of a drop. For example, a continuous flow of collecting medium may be provided, into which the object or objects is/are catapulted.

The solutions shown for handling micro-dissected biological objects according to exemplary embodiments may offer various advantages. For example, they may provide low material consumption, easy automatability, the possibility of a high throughput, a reduced risk relative to contamination, and lower storage costs for consumables. For a plurality of preparation and analysis processes, a considerably more effective overall sequence may be facilitated. Any autoclaving processes of consumer products used in the conventional methods can be dispensed with because, in particular, no collecting vessels or collector substrates provided specially for this are needed. Due to precise liquid management, a high level of accuracy and reliability of investigations and preparations may be achieved.

We claim:

1. A method for handling objects, which comprises:
    locating an object on a carrier; and
    transporting the object by a laser-induced transport process from the carrier to a collecting medium that is in a liquid state and that is held in the form of a drop on a collecting device by at least one of adhesion and surface tension.

2. The method according to claim 1, which further comprises, following the laser-induced transport process, transferring the object with the drop of collecting medium to a target location.

3. The method according to claim 2, which further comprises carrying out the transferring step by conveying of the collecting medium.

4. The method according to claim 2, which further comprises carrying out the transferring step by causing a flow motion of the collecting medium.

5. The method according to claim 2, which further comprises carrying out the transferring step by drop-like dispensing of the collecting medium.

6. The method according to claim 2, which further comprises carrying out the transferring step by sucking the collecting medium.

7. The method according to claim 2, which further comprises:
carrying out the transferring step by moving the collecting device relative to the target location.

8. The method according to claim 2, which further comprises carrying out the transferring step by supplying further collecting medium to the collecting medium with the object.

9. The method according to claim 2, which further comprises executing the transferring step automatically.

10. The method according to claim 1, which further comprises targetedly influencing a shaping of a surface of the collecting medium presented to the carrier with a geometry of the collecting device.

11. The method according to claim 1, which further comprises targetedly influencing a shaping of a surface of the collecting medium presented to the carrier with a surface composition of the collecting device.

12. The method according to claim 1, which further comprises selecting the collecting medium dependent upon a following processing step for the object.

13. The method according to claim 1, which further comprises separating the object from a mass located on the carrier by laser irradiation.

14. The method according to claim 1, which further comprises checking a result of the laser-induced transport process by monitoring the collecting medium.

15. The method according to claim 14, which further comprises carrying out the monitoring based upon optical signal processing.

16. The method according to claim 14, which further comprises carrying out the checking step based upon acoustic signals in the ultrasonic range.

17. A device for handling objects located on a carrier, comprising:
a collecting device having a tip configured to hold a collecting medium in a liquid state in the form of a drop by at least one of adhesion and surface tension and to receive objects located on the carrier;
a holding device shaped to hold the carrier; and
a laser configuration operable to carry out a laser-induced transport process of the objects on the carrier from the carrier to said drop of said collecting medium.

18. The device according to claim 17, further comprising an imaging device operable to produce an image of the carrier.

19. The device according to claim 17, wherein said tip has an opening configured to dispense said drop of said collecting medium.

20. The device according to claim 19, wherein said opening of said tip has an inset having an additional surface to hold said drop of said collecting medium.

21. The device according to claim 17, wherein said collecting device, said holding device, and said laser configuration are configured to handle the objects on the carrier and transport the objects by said laser-induced transport process from the carrier to said liquid collecting medium.

22. A method for handling objects, which comprises:
locating an object on a carrier;
holding a liquid collecting medium in the form of a drop on an object collecting device by at least one of adhesion and surface tension;
transporting the object from the carrier to the liquid collecting medium by separating the object from a mass located on the carrier with laser irradiation; and
following the laser-induced transport of the object, transferring the drop of collecting medium with the object to a target location by dispensing the drop of collecting medium.

* * * * *